United States Patent [19]

Cook et al.

[11] 4,017,515

[45] Apr. 12, 1977

[54] α-(ETHERIFIED OXIMINO) CARBOXYLIC ACIDS AND ACID CHLORIDES

[75] Inventors: Martin C. Cook, Liverpool; Gordon I. Gregory, Chalfont St. Peter; Janice Bradshaw, Harow, all of England

[73] Assignee: Glaxo Laboratories Limited, Greenford, England

[22] Filed: Sept. 30, 1975

[21] Appl. No.: 618,167

Related U.S. Application Data

[60] Division of Ser. No. 304,524, Nov. 7, 1972, Pat. No. 3,971,728, which is a continuation-in-part of Ser. No. 252,666, May 12, 1972, abandoned.

[30] Foreign Application Priority Data

| | | |
|---|---|---|
| May 14, 1971 | United Kingdom | 15082/71 |
| Oct. 1, 1971 | United Kingdom | 45884/71 |
| May 12, 1972 | United Kingdom | 15082/72 |
| Oct. 25, 1972 | United Kingdom | 49255/72 |

[52] U.S. Cl. .............. 260/332.3 R; 260/294.8 R; 260/294.8 C; 260/294.8 D; 260/294.9; 260/295 CA; 260/295 AM; 260/296 AE; 260/329 HS; 260/329 S; 260/329 F; 260/329 AM; 260/330.5; 260/332.2 A; 260/332.2 C; 260/332.2 R; 260/332.3 P; 260/332.3 H; 260/332.5; 260/346.2 R; 260/347.2; 260/347.3; 260/347.4; 260/347.7

[51] Int. Cl.$^2$ .......................... C07D 333/16

[58] Field of Search .............. 260/347.7, 332.3 R, 260/329 AM, 332.2 R, 330.5, 326.2, 326.5 L, 296 AE, 347.2, 347.7, 294.8 R, 294.8 C, 294.8 D, 294.9, 295 CA, 295 AM, 326.5, 326.35, 326.36, 326.5 S, 326.5 SA, 326.5 SM, 326.6 Z, 329 S, 329 HS, 329 F, 332.2 C, 332.2 A, 332.3 P, 332.3 H, 332.5, 346.2 R, 347.3, 347.4

[56] References Cited

UNITED STATES PATENTS

| | | | |
|---|---|---|---|
| 3,546,219 | 12/1970 | Long et al. | 260/243 |
| 3,573,294 | 3/1971 | Long et al. | 260/243 |

OTHER PUBLICATIONS

Moses et al., Arkiv for Kemi, 22, No. 33 pp. 451–467 (1964).

*Primary Examiner*—Gerald A. Schwartz
*Attorney, Agent, or Firm*—Bacon & Thomas

[57] ABSTRACT

α-(Etherified oximino)carboxylic acids, represented by the formula:-

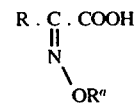

where R is hydrogen or an organic group having 1–20 carbon atoms and $R''$ is an etherifying monovalent organic group having 1–16 carbon atoms linked to the oxygen atom through a carbon atom, and the corresponding acid chlorides, are useful intermediates in the preparation of highly active, highly β-lactamase-stable 7β-[α-(etherified oximino)acylamido]-ceph-3-em-4-carboxylic acid antibiotics. The compounds are syn isomers or exist as mixtures of syn and anti isomers containing at least 75% of the syn isomer.

15 Claims, No Drawings

α-(ETHERIFIED OXIMINO) CARBOXYLIC ACIDS AND ACID CHLORIDES

CROSS REFERENCE TO RELATED APPLICATIONS

This application is a division of pending application Ser. No. 304,524, filed Nov. 7, 1972, now U.S. Pat. No. 3,971,778 which in turn is a continuation-in-part of application Ser. No. 252,666, filed May 12, 1972 and now abandoned.

This invention concerns a new class of carboxylic acids and derivatives thereof. More particularly the invention relates to α-(etherified oximino) carboxylic acids and various derivatives thereof, which compounds are of value as intermediates in the preparation of a range of cephalosporin and penicillin antibiotics.

According to one embodiment of the present invention, therefore, there are provided acids of general formula

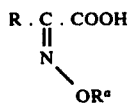
(I)

(wherein R is hydrogen or an organic group and $R^a$ is an etherifying monovalent organic group linked to the oxygen atom through a carbon atom) and salts, esters and amideforming derivatives thereof.

As will be apparent from formula I, the compounds of the invention have the syn isomeric form as regards the configuration of the group $OR^a$ with respect to the carboxy group, although the invention also embraces mixtures of syn and anti isomers wherein the syn isomer predominates, e.g. mixtures containing at least 75%, preferably at least 90%, of the syn isomer. The configuration of the compounds of the invention has been assigned on the basis of the work of Ahmad and Spencer as reported in Can. J. Chem., 1961, 39 1340.

The compounds of the invention, especially acids (I) and their salts and amide-forming derivatives, are of value as intermediates in the preparation of cephalosporin antibiotics possessing at the 7β- position a syn-β-(etherified oximino) acylamido group of formula

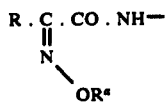

(wherein R and $R^a$ have the above-defined meanings), such cephalosporin compounds and their preparation being described in greater detail in our copending application Ser. No. 304,524, filed Nov. 7, 1972 as a continuation-in-part of our application Ser. No. 252,666, filed May 12, 1972 and now abandoned.

Ester derivatives of acids of formula I are principally of value as intermediates in the synthesis of free acids (I) and their salts, as described in greater detail hereinafter.

Salts of acids of formula I embraced by the invention include alkali metal salts such as the sodium and potassium salts. Esters of acids of formula I embraced by the invention include the methyl esters.

Preferred amide-forming derivatives of acids of formula I according to the invention are the corresponding acid halides, especially the acid chlorides and acid bromides.

Other amide-forming derivatives of acids of formula I in accordance with the invention include symmetrical anhydrides; mixed anhydrides, e.g. with pivalic acid, a phosphorus acid (e.g. phosphoric or phosphorous acids), sulphuric acid, an aliphatic or aromatic sulphonic acid (e.g. p-toluene sulphonic acid) or formed with a lower alkyl haloformate; and activated esters, e.g. compounds of the general formula

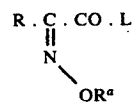
(II)

(where R and $R^a$ have the above-defined meanings and L is an azido, oxysuccinimido, oxybenzotriazolo, pentachlorophenoxy or p-nitrophenoxy group).

The group $R^a$ in the above formulae may be a group having a carbon atom with one free valency so that it forms the desired ether group with the adjacent oxygen atom. The group $R^a$ desirably contains not more than 16 carbon atoms.

$R^a$ may thus be, for example, an alkyl group containing 1–16 carbon atoms, particularly a lower alkyl group containing 1–8 carbon atoms, e.g. a methyl, ethyl, n-propyl, iso-propyl, n-butyl, iso-butyl, sec-butyl, t-butyl, octyl or dodecyl group; an alkenyl group containing 2–16 carbon atoms, preferably 2–8 carbon atoms, e.g. a vinyl, allyl, isopropenyl, or dimethylallyl group; an alkynyl group containing 2–16 carbon atoms, preferably 2–8 carbon atoms, e.g. a propynyl group such as propargyl; a cycloalkyl group containing 3–7 carbon atoms, e.g. a cyclopropyl, cyclopentyl or cyclohexyl group; a cycloalkenyl group containing 4–7 carbon atoms, e.g. a cyclopentenyl, cyclohexenyl, cyclopentadienyl group or cyclohexadienyl; a carbocyclic aryl group, e.g. a phenyl or naphthyl group; a heterocyclic group containing at least one hetero atom selected from oxygen, nitrogen and sulphur, e.g. a pyridyl, pyrimidyl, furyl, thienyl, thiazolyl, thiadiazolyl, diazolyl, triazolyl, tetrazolyl, thiatriazolyl, oxazolyl, oxadiazolyl, benzimidazolyl, benzoxazolyl or purinyl group; or a carbocyclic or heterocyclic aryl lower alkyl group in which the lower alkyl portion contains 1–4 carbon atoms, e.g. a benzyl, phenethyl, diphenylmethyl, triphenylmethyl, thienylmethyl such as thien-2-ylmethyl, furylmethyl such as furfuryl, pyridylmethyl, or pyrrolylmethyl group.

In general $R^a$ may be unsubstituted or may carry one or more substituents such as, for example, hydroxy; alkoxy, e.g. methoxy, ethoxy, n-propoxy or iso-propoxy, as in, for example, methoxymethyl or 1-ethoxyethyl; aryloxy, e.g. phenoxy; aralkoxy, e.g. benzyloxy; mercapto; alkylthio, e.g. methylthio or ethylthio; arylthio; aralkylthio; amino as in, for example, 2-aminoethyl; substituted amino, e.g. methylamino, ethylamino or dimethylamino; halo, e.g. chloro or bromo, as in, for example, 2-bromoethyl; nitro; azido; carboxy; esterified carboxy, e.g. lower alkoxy carbonyl such as methoxycarbonyl or ethoxycarbonyl, or benzyloxycarbonyl; formyl; acyl, e.g. acetyl, propionyl or benzoyl; acyloxy e.g. acetoxy, propionyloxy or pivaloyloxy; cyano; phthalimido; acylamido, e.g. acetamido or benzamido; alkoxycarbonylamino, e.g. methoxycarbonylamino or ethoxycarbonylamino; or aralkoxycarbonylamino, e.g. benzyloxycarbonylamino.

Where R in the above formulae is other than hydrogen it may be chosen from the following list, which is not intended to be exhaustive:- i. $R^u$, where $R^u$ is aryl (carbocyclic or heterocyclic), cycloalkyl, substituted aryl, substituted cycloalkyl, cycloalkadienyl, or a non-aromatic or mesionic group. Examples of this group include phenyl; naphthyl e.g. naphth-1-yl; phenyl or naphthyl substituted by halo (e.g. chloro or bromo as in o-chlorophenyl), hydroxy, lower alkyl (e.g. methyl), nitro, amino, lower alkylamino (e.g. methylamino), diloweralkylamino (e.g. dimethylamino), lower alkanoyl (e.g. acetyl), lower alkanoylamido, lower alkoxy (e.g. methoxy or ethoxy), or lower alkylthio (e.g. methylthio); 5- or 6- membered heterocyclic groups containing at least one hetero atom selected from S, N and O, e.g. thien-2-yl, thien-3-yl, furyl such as fur-2-yl, pyridyl such as pyrid-3-yl, pyrrolyl, N-substituted pyrrolyl (e.g. N-methylpyrrolyl), isothiazolyl, thiadiazolyl, oxadiazolyl, 3- or 4-isoxazolyl, substituted 3- or 4-isoxazolyl (e.g. 3-aryl-5-methylisoxazol-4-yl, the aryl group being e.g. phenyl or halophenyl) or sydnone; fused heterocyclic groups containing at least one hetero atom selected from S, N and O, for example benzothienyl (e.g. benzothien-3-yl), benzofuryl or indolyl; cyclohexyl; cyclopentyl; and cyclohexadienyl.

ii. $R^u(CH_2)_mQ_n(CH_2)_p$ where $R^u$ is as defined under (i) and m is 0 or an integer from 1 to 4, n is 0 or 1, p is an integer from 1 to 4 and Q is S, O or $NR^b$ wherein $R^b$ is hydrogen or an organic group (e.g. alkyl such as methyl or aryl such as phenyl). Examples of this group include methyl, ethyl or butyl substituted by the various specific $R^u$ groups listed under (i) e.g. benzyl and the appropriate substituted benzyl groups.

iii. $C_nH_{2n+1}$ wherein n is an integer from 1 to 7. The group may be straight or branched and, if desired, may be interrupted by an oxygen or sulphur atom or the group $NR^b$ wherein $R^b$ is hydrogen or an organic group (e.g. alkyl such as methyl or aryl such as phenyl) and/or may be substituted by a cyano, carboxy, alkoxycarbonyl, hydroxy or carboxycarbonyl (HOOC.CO.) group or by a halogen atom. Examples of such groups include hexyl, heptyl, butylthiomethyl, cyanomethyl and trihalomethyl.

iv. $C_nH_{2n-1}$ where n is an integer from 2 to 7. The group may be straight or branched and, if desired, may be interrupted by an oxygen or sulphur atom or the group NR wherein R is hydrogen or an organic group e.g. alkyl such as methyl or aryl such as phenyl. Examples of such groups are vinyl and propenyl.

v. $C_nH_{2n-3}$ where n is an integer from 2 to 7. An example of such a group is ethynyl.

vi. Miscellaneous carbon-linked organic groups including cyano, amido and lower alkoxycarbonyl.

Preferred compounds in accordance with the invention, by virtue of the valuable antibiotic properties exhibited by cephalosporin and/or penicillin antibiotics containing respectively a 7β- or 6β-[α-(etherified oximino) acylamido]to side chain derived therefrom include acids of general formula

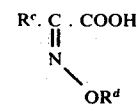

$$R^c . \underset{\underset{OR^d}{\overset{\displaystyle N}{\diagdown}}}{\overset{\|}{C}} . COOH \qquad (III)$$

(where $R^c$ is phenyl; naphthyl; thienyl; furyl; benzothienyl; benzofuryl; pyridyl; or any of the preceding groups substituted by one or more of fluoro, chloro, bromo, iodo, hydroxy, lower alkyl, nitro, amino, lower alkylamino, di(lower alkyl) amino, lower alkanoyl, lower alkanoylamido, lower alkoxy, lower alkylthio and carbamoyl; and $R^d$ is lower alkyl; lower cycloalkyl; carbocyclic or heterocyclic aryl lower alkyl; or any of these groups substituted by one or more of hydroxy, carboxy, esterified carboxy, amido, cyano, lower alkanoyl, amino, substituted amino, fluoro, chloro, bromo, iodo and lower alkoxy) and their salts, esters and amide-forming derivatives.

A particularly preferred class of acids falling within the scope of formula III consists of those compounds having the general formula $$R^e . \underset{\underset{OR^f}{\overset{\displaystyle N}{\diagdown}}}{\overset{\|}{C}} . COOH \qquad (IV)$$

wherein $R^e$ is phenyl, naphthyl, thienyl, furyl, benzothienyl or benzofuryl and $R^f$ is $C_{1-4}$ alkyl, benzyl, phenethyl, thienylmethyl or furylmethyl.

In this specification and the appendant claims the term "lower" as used to qualify groups containing an alkyl moiety (as in, for example, lower alkyl, lower alkoxy or lower alkanoyl) indicates that the alkyl moiety of said group contains 1-6 carbon atoms. The term "lower cycloalkyl" designates cycloalkyl groups containing 3-7 carbon atoms.

Acids of general formula I and their salts and esters may be prepared in accordance with a further embodiment of the invention by either (A) reacting a glyoxylic acid of formula $$R.CO.COOH \qquad (V)$$

(where R has the above-defined meaning), or an ester thereof, with a compound of formula $$R^a.ONH_2 \qquad (VI)$$

(where $R^a$ has the above-defined meaning), or a salt (e.g. the hydrochloride) thereof; or (B) reacting a compound of general formula $$R . \underset{\underset{OH}{\overset{\displaystyle N}{\diagdown}}}{\overset{\|}{C}} . COOH \qquad (VII)$$

(where R has the above-defined meaning), or, more preferably, an ester thereof, with an etherifying agent serving to introduce the desired $R^a$ group; and (C) recovering the desired compound, if necessary after separation of syn and anti isomers, hydrolysis of an ester product to give the corresponding acid, and/or conversion of an acid to a salt thereof.

The etherification of acids of formula VII or ester derivatives thereof may be effected by, for example, reaction of the acid or ester with an organic halide, sulphate or sulphonate (e.g. a compound of formula $R^aJ$ where $R^a$ has the above-defined meaning and J is halogen, sulphate or sulphonate such as tosylate); a diazoalkane (e.g. diazomethane); an alkyl fluorosulphonate (e.g. methyl fluorosulphonate); an alkyloxonium tetrafluoroborate (e.g. a trialkyloxonium tetrafluoroborate such as triethyloxonium tetrafluoroborate) or diphenyliodonium bromide. Such reactions with a diazo compound, fluorosulphonate or tetrafluoroborate may require assistance, e.g. with a Lewis acid such as $BF_3$.

Separation of the syn and anti isomers of an acid or ester product may be effected by, for example, crystallisation, chromatography or distillation, followed when necessary by hydrolysis of an ester derivative.

When a 2-alkoxyimino-2-arylacetic ester product is obtained, e.g. by reaction of an ester of an acid of formula V or VII wherein R is a carbocyclic or heterocyclic aryl group to yield a product in which $R^a$ is an alkyl group, or by esterification of 2-alkoxyimino-2-arylacetic acid product, e.g. using diazomethane, separation of the syn and anti isomers may be effected by selective hydrolysis of the ester, since the less sterically hindered anti isomer tends to saponify more rapidly and may thus be removed as the free acid, leaving purified syn ester which may then be isolated and, if desired, hydrolysed to yield the corresponding syn acid.

Syn and anti isomers may be distinguished by appropriate techniques such as ultraviolet spectroscopy, thin layer or paper chromatography or nuclear magnetic resonance spectroscopy.

Amide-forming derivatives of acids of formula I may be prepared by any convenient method. Thus, for example, acid chlorides and acid bromides may be prepared by reacting an acid (I) or a salt thereof with a chlorinating or brominating agent, followed if necessary by separation of syn and anti isomers. Representative chlorinating agents which may be used in this process include phosphorus pentachloride, thionyl chloride and oxalyl chloride. We prefer to prepare acid chlorides by reaction of the sodium or potassium salt of an acid (I) with oxalyl chloride, since under these conditions isomerisation is minimal.

It will be appreciated that when converting an acid (I) to an amide-forming derivative, any amino groups present in R or $R^a$ should desirably be protected to avoid unwanted side reaction.

The following examples illustrate the invention. All temperatures are in °C.

Preparation 1

Benzo[b]-thien-2-ylglyoxylic acid and Benzo[b]-thien-3-ylglyoxylic acid

A mixture of 2- and 3-acetylbenzo[b]-thiophene (ca. 1:1) (11.0 g.) in pyridine (80 ml.) was warmed to 60° with vigorous stirring and selenium dioxide (9.92 g.) was added portionwise. The mixture was heated to 110° C and an exothermic reaction occurred, the temperature rising to 120°. The reaction was stirred at 90° for 45 mins. and then left to cool. Water (80 ml.) was added and the mixture filtered through a kieselguhr pad. The pyridine was removed by evaporation and the aqueous residue again filtered. The filtrate was acidified to pH 2 under ether with 40% orthophosphoric acid (40 ml).

The aqueous phase was extracted with ether and the ether fractions were combined, washed with water and dried. Evaporation gave an orange crystalline solid (11.0 g., 86%). Crystallisation from benzene (100ml) gave bright yellow crystals of benzo[b]-thien-2-ylglyoxylic acid (2.3 g. 18%), m.p. 175.9°, $\lambda_{max.}$ (EtOH), 233, 247,[infl. 308 nm. ($\epsilon$ 11,400; 7,200; 14,600), $\tau$ (DMSO-$d_6$) values include 1.83 (C-4 and C-7 protons, 1.42 (C-3 proton), 2.40 (C-5 and C-6 protons).

The mother liquor was concentrated to an orange oil which crystallised on standing (8 g.). Recrystallisation from benzene (20 ml.) gave pale yellow needles of benzo-[b]-thien-3-ylglyoxylic acid (1.6 g., 12.5%), m.p. 92°–93°,$\tau$ (DMSO-$d_6$) values include 0.83 (C-2 proton), 1.32 (C-4 proton), 1.79 (C-7 proton), 2.40 (C-5 and C-6 protons), $\lambda_{max.}$ (EtOH) 235, 310.5 nm ($\epsilon$ 11,200 and 7,400).

Preparation 2 a. N-(Thien-2-ylmethoxy)phthalimide

Anhydrous potassium carbonate (11.04 g.) was added to a stirred suspension of N-hydroxyphthalimide (17.12 g.) in dry dimethyl sulphoxide (200 ml.). A brown colour developed, 2-chloromethylthiophene (28.5 g.) was added dropwise and the mixture was stirred for 16 hr., during which time the colour disappeared. The suspension was poured into water (800 ml.) and cooled to 5°. The white precipitate was filtered off, and recrystallised from ethanol to give colourless needles of N-(thien-2-ylmethoxy)phthalimide (23.4 g., 83%), m.p. 129.7°–130.0° $\tau$ values (DMSO-$d_6$) are 4.58 ($CH_2$), 2.28, 2.68, 2.90 (thienyl protons), 2.08 (phthalimide protons).

b. Thien-2-ylmethoxyamine hydrochloride

A mixture of N-(thien-2-ylmethoxy)phthalimide (22.4 g) 100% hydrazine hydrate (5 g) and ethanol (600 ml.) was heated under reflux for two hours. Initially, a yellow solution was formed, but soon solid began to precipitate. The mixture was cooled, then acidified with concentrated hydrochloric acid (12 ml.). The precipitated phthalhydrazide was filtered off and washed with ethanol (3 × 50 ml.) and water (100 ml.). The combined filtrate and washings were evaporated to dryness, and the residue, suspended in water, was basified with 2N sodium hydroxide solution. The basic mixture was extracted with ether, and the combined extracts were washed (water, saturated brine), dried, and saturated with dry hydrogen chloride. The precipitated solid was collected and well washed with ether to give thien-2-ylmethoxyamine hydrochloride, (12.45 g., 87%), m.p. 157.1° – 157.5°. A sample recrystallised from ethanol/ether had m.p. 161.7 – 162.1 $\tau$ values (DMSO-$d_6$) include 4.69 ($CH_2$), 2.30, 2.72, 2.90 (thienyl protons)

Preparation 3 a. N-(Fur-2-ylmethoxy)phthalimide

To a stirred mixture of N-hydroxyphthalimide (41 g.), anhydrous potassium carbonate (26.4 g.) and dry dimethyl sulphoxide (400 ml.) was added 2-chloromethylfuran (freshly prepared, but undistilled, from 46.2 g. furfuryl alcohol according to the method of W. R. Kirner JACS, 1928, 50, 1955). The mixture was stirred for 18 hr., then poured into water (1.5 l). The precipitated solid was filtered off, washed well with water, and recrystallised from ethanol to give N-(fur-2-ylmethoxy)phthalimide (42.8 g., 70%), m.p. 145.3° – 146.2° $\tau$ values (DMSO-$d_6$) are 4.80 ($CH_2$), 2.22, 3.30, 3.50 (furyl protons) 2.08 (phthalimide protons).

b. Fur-2-ylmethoxyamine Hydrochloride

100% Hydrazine hydrate (20 ml.) was added to a stirred solution of N-(fur-2-ylmethoxy)phthalimide (42.0 g.) in methylene chloride (600 ml.). A copious precipitate formed immediately, and the mixture was stirred for 45 min. 5N Ammonium hydroxide solution (500 ml.) was added to dissolve the precipitate, the two layers were separated, and the aqueous layer was washed twice with methylene chloride. The combined methylene chloride extracts were washed (saturated brine) and dried. Methylene chloride was evaporated off, and the residual liquid was dissolved in ether (250 ml.). Dry hydrogen chloride was passed into this solution for one hour. The precipitated solid was filtered off, washed with ether, dried, and recrystallised from isopropanol to give fur-2-ylmethoxyamine hydrochloride (12.89 g., 50%), m.p. 135°–136° (decomp) $\tau$ values (DMSO-$d_6$) include 4.87 ($CH_2$), 2.20,. 3.27, 3.44 (furyl protons).

Preparation 4

Cyclopentyloxyamine hydrochloride

A mixture of bromocyclopentane (14.9 g), N-hydroxyphthalimide (16.3 g), triethylamine (15 ml), and dimethylformamide (30 ml) was stirred for 16 hours, then poured into water (500 ml). The oily mixture was extracted with ethyl acetate, and the combined extracts, after washing (water), drying, and removal of solvent gave a white solid. This solid was recrystallised from ethanol to give N-cyclopentyloxyphthalimide (11.37 g, 49%); m.p. 81.2°–82.5°; $\nu_{max.}$ ($CHBr_3$) include 1780, 1720 $cm^{-1}$ (CO-N-CO), 970 $cm^{-1}$ (>N-O-<CH); $\tau$ values (DMSO-d6) 2.08 (4 Ar-H), 5.12 (cyclopentyl 1-H), 8.18 (4-$CH_2$).

A mixture of N-cyclopentyloxyphthalimide (11 g), 100% hydrazine hydrate (2.6 g), and ethanol (30 ml) was heated under reflux for 5 minutes. Concentrated hydrochloric acid (6 ml) was added to the mixture, which was heated under reflux for a further 5 minutes. Water (20 ml) was added to the mixture, which was cooled to room temperature, and filtered. The filtrate was evaporated to dryness, ethanol (50 ml) was added to the residue, and a small amount of insoluble material was filtered off. The filtrate was evaporated to dryness, and the residue was recrystallised from ethanol/ether to give cyclopentyloxyamine hydrochloride (6.28 g, 96%), m.p. 156.9°.

Preparation 5 t-Butoxycarbonylmethoxyamine t-Butyl chloroacetate (13.0g, prepared according to Org. Synth., Coll.Vol. 4, 263) was added dropwise to a stirred mixture of N-hydroxyphthalimide (14.2g), triethylamine (23.0g), and dimethylformamide (30ml), and the resulting mixture was stirred for 4 hr. The mixture was poured into water (500 ml), and the precipitated solid was collected, washed with water, and dried. Recrystallisation from ethanol gave N-t-butoxycarbonylmethoxyphthalimide (17.26g, 72%); m.p. 145.6°; $\tau$ values (DMSO-d6) 2.09 (4 Ar-H), 5.28 ($CH_2$), 8.56 ($Bu^t$).

A solution of N-t-butoxycarbonylmethoxyphthalimide (21g) in methylene chloride (250ml) was treated with 100% hydrazine hydrate (7.6ml) in methanol (15ml), and the mixture was stirred for 1.5 hr. 5N-Ammonia solution was added to dissolve the precipitated solid. The organic layer was separated, and the aqueous layer was further extracted with methylene chloride. The combined extracts were washed with water, dried, and evaporated to give a pale-yellow solid. To this was added ether, the mixture was filtered, and the filtrate evaporated to give t-butoxycarbonylmethoxyamine as a pale yellow liquid, (8.88g, 80%); $\nu_{max.}$ (Nujol) includes 3330, 3260 $cm.^{-1}$ ($NH_2$), 1742 $cm.^{-1}$ (-$COOBu^t$); $\tau$ values (DMSO-d6) are 3.75 (–$NH_2$), 5.96 ($CH_2$) 8.55 ($Bu^t$).

Preparation 6 a. Methyl 1-Benzyloxymethylpyrrol-2-ylglyoxylate

Methyl pyrrol-2-ylglyoxylate (306 mg) in diglyme was treated with sodium hydride (63mg) and stirred at room temperature for 3 hr. Benzyloxymethyl chloride (376mg) was added and the mixture stirred at room temperature for a further 3 hr. The suspension was filtered and the filtrate evaporated. The residue, in ether, was washed with sodium bicarbonate solution, water and dried. Evaporation gave the crude product as a brown oil (530mg). Purification by preparative thin-layer chromatography gave the title compound as a colourless oil (250 mg,46%); $\tau$ values (DMSO-d6) include 6.10 (—$CH_3$), 4.20 (N-$CH_2$—). 5.47 (—$OCH_2$—), 2.70 (—Ph).

b. N-Benzyloxymethylpyrrol-2-ylglyoxylic acid

Crude methyl 1-benzyloxymethylpyrrol-2-ylglyoxylate (10g) in methanol (150ml) was treated with sodium hydroxide solution (N: 40 ml) at room temperature for 1 hr. Thin-layer chromatography showed complete hydrolysis. Hydrochloric acid (2N: 20 ml) was added and the methanol was removed by evaporation. The residue was shaken with sodium bicarbonate solution and ether. The aqueous layer was acidified under ether and the ether extract was washed with water and dried. Evaporation gave the acid as an orange oil (4.5g,55%); this material was used directly to make the syn-methoxime described in Example 33.

EXAMPLE 1

2-Methoxyimino-2-phenylacetic acid (syn isomer)

A solution of sodium (5 g.) in dry methanol (100 ml) was added to a solution of 0-methylhydroxylamine hydrochloride (15 g.) in dry methanol (100 ml) until neutral to phenolphthalein. The precipitated sodium chloride was removed by filtration, and the filtrate added to a solution of phenylglyoxylic acid (25 g.) in dry methanol (100 ). The solution was refluxed for 2 hours, cooled, and evaporated to an oil, which was dissolved in ether (200 ml), refiltered and evaporated to an oil (32.9 g.). This was crystallised from petroleum spirit, (bp. 60°–80°) producing a white solid (19.61 g.) and oil (3.9 g.).

The solid (17.8 g.) and the oil (3.9 g.) were combined (21.7 g.) and methylated with ethereal diazomethane, producing an oil (24.2 g.). This was purified by chromatography on silica gel (600 g.), producing syn-methyl 2-methoxyimino-2-phenylacetate as an oil (13.6 g. 55%), $\lambda_{max.}$ (EtOH) 259 nm ($\epsilon$ 10,400) and the corresponding anti isomer as the slower component.

The syn ester (13.6 g.) was dissolved in methanol (100 ml) and 2N-sodium hydroxide solution (22 ml.) was added. The solution was stirred at room temperature for 40 hours, and the pH adjusted to 7 with 2N-hydrochloric acid. Methanol was removed by evaporation, water (150 ml.) was added, and the solution acidified to pH 1.5 with 2N-hydrochloric acid. The mixture was extracted with ethyl acetate (3 × 100 ml), the organic extracts were combined, dried and evaporated to give a white solid (11.13 g.) which was crystallised from petroleum spirit (bpt. 60°–80°): benzene, producing syn-2-methoxyimino-2-phenylacetic acid as a white solid (10.02 g.). m.p. 96°–97°, $\lambda_{max}$. (EtOH) 255 nm, ($\epsilon$ 13,200), $\tau$ (CDCl$_3$) values include 2.2–2.8 (Ph), 5.92 (CH$_3$).

EXAMPLE 2

2-Methoxyimino-2-(thien-2-yl)acetic acid (syn isomer)

A solution of methoxyamine hydrochloride (5.85 g.) in dry methanol (60 ml.) was neutralised (phenolphthalein) with a solution of sodium methoxide in methanol [from sodium (2.5 g.) and dry methanol (50 ml.)]. The precipitated sodium chloride was removed by filtration, and the filtrate was added to a solution of thien 2-ylglyoxylic acid (10 g.) in dry methanol (60 ml.). The resulting solution was refluxed for 1 hour, cooled, and evaporated to an oil. Ether (100 ml.) was added, the mixture was filtered, and the filtrate was evaporated to an oil (13.06 g.).

The oil (12.5 g.) was dissolved in ether (50 ml.) and an ethereal solution of diazomethane was added until a permanent yellow colour remained. The excess diazomethane was destroyed by leaving the solution in sunlight for 1 hour. Evaporation of this solution produced an oil (13.2 g.).

The oil (10.33 g.) was purified by preparative plate chromatography (Kieselgel PF$_{254\ +\ 366}$) developing three times with 75% petroluem spirit (b.p. 60°–80°) in benzene, producing methyl 2-methoxyimino-2-(thien-2-yl)-acetate (syn isomer) (3.44 g., 27%), $\lambda_{max}.^{EtOH}$ 290 nm ($\epsilon$11,250), $\lambda_{inf.}$ 271 nm ($\epsilon$ 5,400) $\nu_{max}$. (CHBr$_3$) 1738 and 1230 cm$^{-1}$ (CO$_2$Me). $\tau$ values (CDCl$_3$) include 6.06 (s, CO$_2$Me), 5.78 (s, OCH$_3$), followed by the corresponding anti isomer and further fractions which were isomeric mixtures.

2N-Sodium hydroxide (8.27 ml.) was added to a solution of methyl 2-methoxylimino-2-(thien-2-yl)-acetate (syn-isomer) (3.28 g.) in methanol (50 ml.) and the solution was stirred at room temperature for 18 hours. Water (20 ml.) was added and the solution was evaporated to remove methanol, and then washed with ethyl acetate. The pH of the solution under ethyl acetate (50 ml.) was altered to 2 with 2N-hydrochloric acid. The layers were separated and the aqueous phase was extracted with ethyl acetate. The organic extracts were combined, dried, and evaporated to a white solid (2.58 g.). This was crystallised from cyclohexane, producing the title compound (2.23 g., 73%), m.p. 105.5°, $\lambda_{max}.^{EtOH}$ 289 nm ($\lambda$ 10,100), $\lambda_{inf.}$ 262 and 271 nm. ($\epsilon$ 7,750 and 8.150), $\tau$ (CDCl$_3$) values include 0.32 (OH) and 5.92 (OCH$_3$).

EXAMPLE 3

2-t-Butoxyimino-2-(thien -2-yl)acetic acid (syn isomer)

A solution of thien-2-ylglyoxylic acid (6.2g.) and sodium bicarbonate (3.36g.) in water (100 ml.) was added dropwise to a stirred solution of t-butoxyamine hydrochloride (5.65 g.) and sodium bicarbonate (3.78g.) in water (100 ml.) at 0°–5° and the mixture was stirred at room temperature for 18 hr. The mixture was acidified with 2N hydrochloric acid to pH 2.0 and extracted with ethyl acetate. The combined extracts were washed with water, dried and concentrated to give a solid (9.75 g.). Recrystallisation from petroleum (b.p. 60°–80°) gave the title compound (4.0 g., 44%), m.p. 106°–107°, $\lambda_{max}.$(EtOH) 290 nm ($\epsilon$11,600), $\tau$ (CDCl$_3$) values include 2.46, 2.66, 2.98 (d doublets, thienyl protons), 8.60 (C(CH$_3$)$_3$).

EXAMPLE 4

2-Ethoxyimino-2-phenylacetic acid (syn isomer)

Ethoxamine hydrochloride (4.0 g.) and phenylglyoxylic acid (6.0 g.) were dissolved in water (50 ml.), and the resulting solution was basified to pH 4.5, and stirred at this pH for 15 hr. Acidification and extraction of the mixture gave, after evaporation of the ethyl acetate, a mixture of syn and anti 2-ethoxyimino-2-phenylacetic acids (7.4 g., 94%).

A solution of the mixed acids (4.0 g.) in ether (100 ml.) was treated with an ethereal solution of diazomethane until a yellow colour persisted. Acetic acid was added to destroy excess diazomethane and the ether solution was washed with sodium bicarbonate solution, water, and brine, then dried. Evaporation of the ether gave the methyl esters (4.1 g.) as an orange oil. These were separated on five 40 × 20 cm. preparative plates, eluting with petroluem spirit (b.p. 40°–60°)/ether (3:1). The slower band was eluted with chloroform, and removal of the solvent gave anti-methyl 2-ethoxyimino-2-phenylacetate as a pale-yellow oil. Similar treatment of the faster band gave syn-methyl 2-ethoxyimino-2-phenylacetate (2.45 g.) as a pale yellow oil, $\tau$ (CDCl$_3$) values include 2.3–2.7 (m, Ph), 5.72 (q, CH$_2$), 6.06 (s, OCH$_3$), 8.67 (t, CH$_3$).

The above syn-methyl ester (2.39 g.) in methanol (60 ml.) was treated with sodium hydroxide solution (2N; 12 ml.), and the solution was stirred for 18 hr. The methanol was removed, and the aqueous mixture, after being acidified to pH 1.5, was extracted with ethyl acetate. The washed and dried extracts were evaporated to dryness, and the residue was recystallised from cyclohexane to give syn-2-ethoxyimino-2-phenyl acetic acid (836 mg.), m.p. 77.9°–79.0°, $\lambda_{max}$. (ethanol) 256.5 nm ($\epsilon$ 12,800); $\tau$ (DMSO-d$_6$) values include 2.48 (m, Ph), 5.74 (q, CH$_2$), 8.71 (t, CH$_3$).

EXAMPLES 5–34

2-(Substituted oxyimino)-2-arylacetic Acids (syn isomers)

General Procedures

A mixture of the aryl glyoxyic acid and an excess (10 to 15%) of the substituted oxyamine hydrochloride was suspended in water or aqueous ethanol, stirred, and the pH of the mixture adjusted to between 7 and 8 (Method A) or between 4 and 5 (Method B) with sodium hydroxide solution (N to 10 N). A clear solution at the selected pH range was maintained during the reaction by further additions of sodium hydroxide solution and ethanol as needed. The reaction mixture was kept at room temperature until all of the ketoacid was consumed (it may be necessary to add a further portion of the more volatile alkoxyamines). The progress of the reaction was followed by acidification of an aliquot, extraction with ethyl acetate and thin layer chromatography of the extract on silica plates (developed with a mixture of chloroform; methanol: acetic acid; 18:2:1). The alkoxyiminoacetic acids were less polar than the starting keto-acids. The reaction times were 2 hr. to 2 days. When reaction was complete the pH of the mixture was adjusted to between 7 and 8 and the ethanol (if any) was removed by evaporation. The aqueous mixture was extracted with ether, the extract discarded and the aqueous phase acidified to pH <2 with dilute hydrochloric acid. The mixture was extracted with ethyl acetate, the extract dried and evaporated to give the crude product which was purified by one of the following methods:

a. Crystallisation and recrystallisation (if needed) from a suitable solvent, b. The crude product dissolved in ether was treated with a small excess of a solution of diazomethane in ether. The excess reagent was destroyed with acetic acid and the solution washed with sodium bicarbonate solution and evaporated to give the crude methyl esters. The esters were separated by preparative thick layer chromatography or column chromatography on silica, and then hydrolysed conventionally with alkali to give the pure syn acids, c. The mixture of methyl esters was prepared as in b. and the isomers separated by crystallisation from a suitable solvent and similarly hydrolysed.

These methods were emloyed to prepare the syn-2-(substituted oxyimino)-2-arylacetic acids listed in Table 1:

TABLE 1

$$\underset{\substack{\|\\ N\\ \diagdown\\ OR^a}}{R\diagup^{CO_2H}}$$

| Example No. | R | $R^a$ | Method | Purification | Mp.° | τvalues (solvent) R | $R^a$ | $\lambda_{max.}$ nm (EtOH) | ε | Yield % (before purification |
|---|---|---|---|---|---|---|---|---|---|---|
| 5 | Ph | $C(CH_3)_3$ | A | (a) | 127–129° | 2.2 – 2.7 (DMSO-$d_6$) | 8.62 | 257 | 13,060 | 100 |
| 6 | Ph | $CH_2Ph$ | A | (a) | 103.3° | 2.2–2.7 (CDCl$_3$) | 4.67 (CH$_2$) | 257 | 15,150 | 100 |
| 7 | Ph | $CH_2$-(thien-2-yl) | B | (a) | 110–111° | 2.44 (DMSO-$d_6$) | 4.58 (CH$_2$) 2.92,2.78,2.44 (thien-2-yl). | — | — | — |
| 8 | (thien-2-yl) | $CH_3$ | B | (a) | 108–109° | 2.61 – 2.91 (CDCl$_3$) | 5.92 | 289 | 10,700 | 91 |
| 9 | (thien-2-yl) | $C_2H_5$ | B | (a) | 89.5–91.5° | 2.29,2.76,2.86 (DMSO-$d_6$) | 5.79 (CH$_2$) 8.72 (CH$_3$) | 289.5 | 12,500 | 87 |

| Example No. | R | $R^a$ | Method | Purification | Mp.° | τvalues (DMSO-$d_6$) R | $R^a$ | $\lambda_{max.}$ nm (EtOH) | ε | Yield % (before purification) |
|---|---|---|---|---|---|---|---|---|---|---|
| 10 | (thien-2-yl) | $CH_2Ph$ | B | (a) | 114–115° | 2.29,2.73,2.84 (DMSO-$d_6$) | 2.59 (Ph) 4.77 (CH$_2$) | 290 | 12,300 | 88 |
| 11 | (thien-2-yl) | $CH_2CH_2Br$ | B | (b) | 92.6° | 2.23;2.71;2.83 | 5.54; 6.28 | 289 | 12,200 | 77 |
| 12 | (naphthyl) | $CH_3$ | B | (b) | 98–99° | 1.38 1.8–2.1 2.1–2.5 | 5.9 | 294.5 | 8,100 | 96 |
| 13 | (naphthyl) | $C(CH_3)_3$ | A | (b) | 122–123° | 1.3–1.5 1.3–2.1 2.2–2.5 | 8.62 | 296.5 | 9,300 | 96 |
| 14 | (naphthyl) | $CH_2Ph$ | A | (a) | — | 1.53,1.92, 2.2–2.7 | 2.50 (Ph) 4.64 (CH$_2$) | 294 | 8,300 | 86 |
| 15 | (fur-2-yl) | $CH_3$ | B | (a) | 85–87° | 2.10, 3.18, 3.33 | 6.06 | 275 | 21,500 | 81 |

TABLE 1-continued $$\begin{array}{c} R \diagdown \phantom{xx} \diagup CO_2H \\ C \\ \| \\ N \\ \diagdown OR^a \end{array}$$

| Example No. | R | $R^a$ | Method | Purification (solvent) | Mp° | τ values (DMSO-d6) R | τ values (DMSO-d6) $R^a$ | $\lambda_{max}$ nm (EtOH) | ε | |
|---|---|---|---|---|---|---|---|---|---|---|
| 16 | 2-furyl | C(CH₃)₃ | B | (a) | 110.5–111.5° | 2.12, 3.24, 3.35 | 8.70 | 275.5 | 16,040 | 95 |
| 17 | 2-furyl | CH₂Ph | B | (a) | 104–105.5° | 2.12, 3.19, 3.33 | 2.58 (Ph) 4.75 (CH₂) | 277 | 17,650 | 81 |
| 18 | 4,5,6,7-tetrahydrobenzothienyl | CH₃ | B | (c) | 129–130° | 1.40,1.83, 1.95,2.44 | 5.92 | 233 284 296.5 306.5 | 22,900 10,900 10,500 9,270 | 99 |
| 19 | 4,5,6,7-tetrahydrobenzothienyl | C(CH₃)₃ | B | (a) | 175–176° | 1.88,2.03, 2.3–2.7 | 8.6 | 234 284.5 297 307.5 | 21,900 11,200 10,800 9,400 | 93 |
| 20 | 4,5,6,7-tetrahydrobenzothienyl | CH₃ | B | (a) | 143–144° (dec) | 2.00,2.36, 2.55 | 6.00 | 231 252.5 296.5 | 5,400 7,300 23,600 | 98 |
| 21 | 2-thienyl | CH₂Ph | B | (a) | 103–103.5° | 2.22, 2.32, 2.65 | 2.59 (Ph) 4.76 (CH₂) | 259 | 15,400 | — |
| 22 | 2-furyl | —CH₂-(2-furyl) | B | (a) | 104.8–105.4° | 2.17; 3.25; 3.40 | 4.92 (CH₂) 2.33, 3.5 (furyl protons) | 276 | 16,300 | 97 |
| 23 | 2-furyl | —C₂H₅ | B | (a) | 91–92° | 2.10, 3.19, 3.33 | 5.79, 8.25 | 274.5 | 15,800 | 92 |
| 24 | Ph | n-C₄H₉ | B | (b) | oil | 2.4–2.6 | 5.82, 2.3–2.8, 9.08 | 257 | 11,500 | 100 |
| 25 | Ph | n-C₃H₇ | B | (b) | oil | 2.48 | 5.88, 8.40, 9.09 | 257 | 11,400 | 100 |
| 26 | 2-thienyl | —C₂H₅ | B | (a) | 74.0° | 2.2–2.4, 2.65 | 5.81, 8.75 | 258.5 | 13,800 | 96 |
| 27 | benzofuryl | —C₂H₅ | B | (a) | 125.5–126° | 2.1–2.8, 2.75 | 5.69, 8.71 | 228 inf 290 297 307 | 7,200 22,940 24,600 22,500 | 84 |

| Example No. | R | $R^a$ | Method | Purification (solvent) | Mp° | τ values (DMSO-d6) R | τ values (DMSO-d6) $R^a$ | $\lambda_{max}$ nm (EtOH) | ε |
|---|---|---|---|---|---|---|---|---|---|
| 28 | 2-thienyl | cyclopentyl | B | (b) (cyclohexane) | 7.12 | 2.30, 2.7–3.0 | 5.25, 7.9–8.6 | 291.5 | 10,900 |
| 29 | benzofuryl | —C(CH₃)₃ | B | (a) (cyclohexane) | 124.5–125.5 | 2.1–2.45, 2.45–2.85, 2.78 | 8.66 | 232.5, 296, 307.5 | 6,700; 25,400; 23,500 |
| 30 | 1-methyl-2-pyrrolyl | —CH₃ | B | (a) (benzene) | 114–115 | 3.03, 3.77, 3.92, 6.16 | 6.24 | 286 | 16,200 |
| 31 | 1-methyl-2-pyrrolyl | —C(CH₃)₃ | B | (a) (benzene) | 146–147 | 3.00, 3.75, 3.90, 6.16 | 8.66 | 284 | 16,000 |
| 32 | Ph | cyclopentyl | B | (b) (cyclohexane) | 93.3 | 2.49 | 5.18 8.0–8.6 | 259 | 14,000 |
| 33 | 1-(benzyloxymethyl)-2-pyrrolyl | CH₃ | B | (b) (cyclohexane/benzene) | 84–86 | 2.68(Ph) 2.78, 3.62, 3.78, 4.32, 5.47 | 6.14 | 285 | 12,400 |

TABLE 1-continued $$\begin{array}{c} R \diagdown \diagup CO_2H \\ \| \\ N \\ \diagdown OR^a \end{array}$$

| | | | | | | | | | |
|---|---|---|---|---|---|---|---|---|---|
| 34 | Ph | $CH_2CO_2Bu^t$ | B | (a) (carbon tetrachloride) | 88.5 | 2.47 | 5.32($CH_2$) 8.58($Bu^t$) | 253 | 13,800 |

EXAMPLE 35 a. Methyl 2-(1-ethoxyethoxyimino)-2-(thien-2-yl)acetate (syn-isomer)

To a stirred mixture of methyl 2-hydroxyimino-2-thien-2-yl)acetate (syn-isomer)(3.98 g.) and ethyl vinyl ether (2.5 mls) in ethyl acetate (25 mls) was added phosphorous oxychloride (2 drops). After 20 mins. at 50° the ethyl acetate was washed with saturated sodium bicarbonate solution, dried over sodium sulphate and evaporated to an oil, giving methyl 2-(1-ethoxyethoxyimino)-2-(thien-2-yl)acetate (syn-isomer) (5.7 g; 100%) $\lambda_{max}$. (EtOH) 289 nm ($\epsilon$ 11,700), $\tau$ (CDCl$_3$; 60 MHz) 2.61 (multiplet; thienyl H$_5$), 2.82 to 2.97 (multiplet; thienyl H$_3$ and H$_4$), 4.64 (quartet, J5Hz;

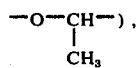

6.06 (singlet, —COOCH$_3$), 6.24 (quartet, J 7 Hz, OCH$_2$), 8.56 (doublet J 5 Hz; CH—CH$_3$), 8.79 (triplet, J 7 Hz; O.CH$_2$CH$_3$).

b. 2-(1-Ethoxyethoxyimino)-2-(thien-2-yl)acetic acid sodium salt (syn-siomer)

1N-Sodium hydroxide (1 equiv.) and enough methanol to form a homogeneous system were added to methyl 2-(1-ethoxyethoxyimino)-2-(thien-2-yl)acetate (syn-isomer) (5.7 g.). After 4 hrs. at 50° the methanol was evaporated and the residue azeotroped with benzene/methanol giving a white solid, 2-(1-ethoxyethoxyimino)-2-(thien-2-yl) acetic acid sodium salt (syn-isomer) (4.6 g, 78.5%),$\lambda_{max}$. (pH 6 buffer) 287.5 nm ($\epsilon$ 10,650), $\tau$ (D$_2$O) values include 2.42 (multiplet; thienyl H$_5$), 2.68 to 2.84 (multiplet; thienyl H$_3$ and H$_4$), 4.63 (quartet, J 5 Hz;

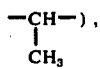

6.21 (quartet, J 7 Hz; —CH$^-$$_2$—CH$_3$), 8.57 (doublet, J 5 Hz;

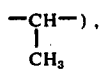

8.82 (triplet, J 7 Hz; —CH$_2$—CH$_3$).

EXAMPLE 36

2-(Thien-2-ylmethoxyimino)-2-(thien-2-yl)acetic acid (syn isomer)

Thien-2-ylmethoxamine hydrochloride (7.37 g.) and thien-2-ylglyoxylic acid (6.24 g.) were dissolved in ethanol (110 ml.) and water (20 ml.). The pH of the solution was adjusted to 5.0, and this solution was stirred for 22 hr. The ethanol was evaporated off, and the aqueous mixture was neutralised, washed twice with ether, then acidified to pH 1.5. The acid mixture was extracted with ethyl acetate. The combined extracts were washed, dried and evaporated to dryness to give a yellow oil (9.2 g., 86%) which crystallised on standing. TLC indicated the solid to be a mixture of isomers. Recrystallisation of this solid several times from cyclohexane effected no separation of isomers. The mixture of acids (5.0 g.) was esterified with diazomethane to give the mixture of methyl esters, as a pale-yellow oil.

To a solution of the mixture of methyl esters (2.14 g.) in methanol (50 ml.) was added 2N sodium hydroxide solution (7.6 ml.). After stirring this solution for 0.5 hr., the solution was neutralised. The methanol was evaporated and the aqueous residue was extracted with ethyl acetate. The extracts were washed, dried, and evaporated to dryness to give a yellow oil (1.0 g.). This oil was dissolved in methanol (25 ml.) and stirred for 18 hr. with 2N sodium hydroxide solution (5 ml.). Methanol was removed by evaporation and the aqueous residue, after washing with ethyl acetate then acidification to pH 1.7, was extracted with ethyl acetate. The extracts were washed, dried, and evaporated to dryness to give a solid (730 mg.). Recrystallisation of this solid twice from cyclohexane gave syn-2-(thien-2-ylmethoxyimino)-2-(thien-2-yl)acetic acid (369 mg.), m.p. 101°–102°, $\lambda_{max}$. (EtOH) 239, 289.5 nm ($\epsilon$ 11,700, 12,300), $\tau$ (DMSO-d$_6$) values include 4.67 (s, CH$_2$).

EXAMPLE 37

2-Benzyloxyimino-2-(benzo[b]-thien-3-yl)acetic acid (syn isomer)

Benzo[b]-thien-3-ylglyoxylic acid (2.27 g) and benzyloxyamine hydrochloride (1.915 g) were dissolved in ethanol (70 ml) and water (30 ml). The solution was adjusted to pH 4.5 with 40% w/v sodium hydroxide solution and stirred at this pH for 2 hr. The solution was stood overnight and adjusted to pH 9 then washed with ether. The aqueous phase was acidified under ethyl acetate and the organic layer was washed with water, saturated brine and dried. Evaporation gave a mixture of syn and anti-isomers as a buff crystalline solid (3.4 g., 99%). The crude acid in ether was treated with excess diazomethane in ether at 0°–5°. The excess reagent was destroyed with acetic acid and the ether solution was washed with sodium bicarbonate, water and dried. Evaporation gave a pale brown oil (3.34 g., 93%). The crude product in methanol (100 ml.) was treated with sodium hydroxide solution (1N, 10 ml) at room temperature for 1 hr. The hydrolysis was followed by thin layer chromatography on silica. Hydrochloric acid (2N 5 ml.) was added to stop the hydrolysis and methanol was removed by evaporation. Ethyl acetate was added and the anti-2-benzyloxyimino-2-(benzo[b]-thien-3-yl)acetic acid was removed by washing with sodium bicarbonate. The ethyl acetate layer was washed with water and dried and evaporated to a pale orange oil (1.99 g., 56%). This was treated in methanol (90 ml.) with sodium hydroxide (1N; 10 ml) at room temperature for 7 hr. A further aliquot of sodium hydroxide (1N; 5 ml) was added and the solution stood for 2 days to complete hydrolysis. The methanol was removed by evaporation and the residue dissolved in ethyl acetate and water. The mixture was adjusted to pH 1.5 and the ethyl acetate layer was washed with water, saturated brine and dried. Evaporation gave yellow crystals (1.82 g. 50%) Crystallisation from a mixture of benzene and cyclohexane gave the title compound as pale orange crystals (1.29 g., 36%), m.p. 120.5°–121°, $\lambda_{max.}$ (EtOH) 232, 285.5, 296.5 306.5 nm. ($\epsilon$22,500, 11,800, 11,500, 10,400), $\tau$ values (DMSO-$d_6$) include 1.90, 1.97, 2.3–2.7 (aromatic protons), 4.64 (CH$_2$ singlet).

Example 38

2-Benzyloxyimino-2-(benzo[b]-thien-2-yl)acetic acid (syn isomer)

Benzo[b]-thien-2-ylglyoxylic acid (3.092 g) and benzyloxyamine hydrochloride (2.72 g.) in ethanol (170 ml.) and water (70 ml.) were adjusted to pH 4.5 with sodium hydroxide (40%). The solution was stirred at this pH at room temperature for 6 hr. Benzyloxyamine hydrochloride (500 mg.,) was added and the solution stood at room temperature overnight. The solution was adjusted to pH 8 and washed with ether. The aqueous phase was acidified under ether to pH 1.5. The ether layer was washed with water and dried. Evaporation gave a cream coloured solid (4.28 g, 91%) as an isomeric mixture.

The crude isomeric mixture was treated in ether with excess diazomethane in ether at 0°–5°. The excess reagent was destroyed with acetic acid and the ether solution was washed with sodium bicarbonate, water and dried. Evaporation gave an oil (4.45 g., 91%). This was dissolved in methanol (140 ml.) and treated at room temperature with sodium hydroxide solution (1N; 14 ml.) for 2¼ hr. Hydrochloric acid (2N, 7 ml.) was added and the alcohol was removed by evaporation. The aqueous phase was partitioned between sodium bicarbonate solution and ether. The ether layer was washed with water and dried, evaporation gave an oil (2.16 g., 44%). This was hydrolysed directly in refluxing methanol (70 ml.) with sodium hydroxide (1N; 7 ml) for 4 hr. The methanol was removed by evaporation and the residue partitioned between water and a little ether. The aqueous layer was acidified under ether to pH 1.5 and the ether layer was washed with water, dried and evaporated to give a pale cream solid (1.97 g, 42%). Crystallisation from a mixture of benzene and cyclohexane gave the title compound as a white crystalline solid, (1.61 g; 35%), m.p. 141°–143° (dec.),$\lambda_{max.}$ (EtOH) 230.5, 253, 297.5 nm ($\epsilon$ 16,400; 7,400; 24,100), $\tau$ (DMSO-$d_6$) values include 2.00, 2.36, 2.55 (aromatic protons), 4.71 (CH$_2$ singlet).

EXAMPLE 39 a. 2-(2-t-Butoxycarbonylaminoethoxyimino)-2-(thien-2-yl) acetic acid (syn-isomer)

N-(t-butoxycarbonyl)-2-bromethylamine (1.12 g.) was added to a solution of the sodium salt of methyl syn-2-hydroxyimino-2-(thien-2-yl)acetate (1.035 g.) in benene: dimethylformamide (2:1 v/v, 30 ml), and the mixture was stirred for 16 hr. Ethyl acetate (50 ml.) was added, and the mixture was washed several times with water, dried, and evaporated to dryness to give methyl syn-2-(2-t-butoxycarbonylaminoethoxyimino)-2-(thien-2-yl)acetate (1.21 g, 75%), $\tau$ (CDCl$_3$) values include 2.62, 2.86, 2.99 (thienyl protons), 5.10 (NH), 6.06 (s, CH$_3$), 8.58 (s,C(CH$_3$)$_3$).

The crude ester (1.1 g) in methanol (20 ml) was treated with 2N sodium hydroxide solution (3.4 ml.), and stood 16 hr. The methanol was evaporated off, and the aqueous residue, after washing with ether, was acidified to pH 2.0, and extracted with ethyl acetate. The extracts were washed (water, saturated brine), dried, and evaporated to dryness. Recrystallisation of the residue from cyclohexane gave the title compound (951 mg., 90%), m.p. 112.8°–114.4°$\lambda_{max.}$ (EtOH) 290.5 nm. ($\epsilon$ 11,600), $\tau$ (DMSO-$d_6$) values include 2.19, 2.6–2.9 (thienyl protons), 3.14 (NH), 8.52 (s, C(CH$_3$)$_3$).

The alkylating agent used for the above process was made as follows b. N-(t-Butoxycarbonyl)-2-bromoethylmine A mixture of t-butyl azidoformate (15.81 g) and triethylamine (30 ml) was added dropwise to a stirred suspension of 2-bromoethylamine hydrobromide (20.5 g.), in methylene chloride (100 ml.). The mixture was stirred for 3 hr., then filtered. The filtrate was concentrated to a small volume, and the residue was distributed between ether and water. The ether layer was dried, then distilled under reduced pressure, collecting the fraction b.p. 92°–94°/0.9 mm as N-(t-Butoxycarbonyl)-2-bromoethylamine (1.756 g.)

EXAMPLE 40

2-(Pyrid-2-ylmethoxyimino)-2-(thien-2 -yl)acetic acid (syn-isomer)

2-Chloromethylpyridine (a 25% solution in toluene, 2.8 ml.) was added to a solution of the sodium salt of methyl syn-2-hydroxyimino-2-(thien-2-yl)acetate (1.035 g.) in benzene:dimethylformamide (30 ml, 2:1, v/v). The solution was stirred for 18 hr., ethyl acetate (50 ml.) was added, and the mixture was washed several times with water, dried and evaporated to dryness to give a dark-green oil (1.4 g.). This oil was chromatographed on two 40 × 20 cm. preparative chromatography plates, eluting with chloroform. The single major band was eluted off the silica with chloroform: ethanol (9:1 v/v) to give after evaporation of the solvent, methyl 2-(pyrid-2-ylmethoxyimino)-2-(thien-2-yl)acetate (889 mg., 47%) (75% syn, 25% anti-isomer). A solution of the crude ester (828 mg.) in methanol (20 ml) and 2N sodium hydroxide solution (3 ml.) was stood 16 hours. After removal of the methanol, the aqueous mixture was acidified to pH 2.0 in the presence of methylene chloride. The acid mixture was extracted with methylene chloride and the extracts were washed (water, brine), dried, and evaporated to dryness. Trituration of the residue with ether gave the title compound (210 mg, 27%), m.p. 152.1° – 152.9°, $\lambda_{max}$ (EtOH) 260.5, 266, 289 nm ($\epsilon$ 12,300; 12,000; 11,700), $\tau$ (DMSO-$d_6$) values include 4.66 (singlet, CH$_2$).

EXAMPLE 41

2-n-Butoxyimino-2-(thien-2-yl)acetic acid (syn-isomer)

1-Bromobutane (0.6 ml.) was added to a solution of methyl syn-2-hydroxyimino-2-(thien-2-yl)acetate sodium salt (prepared by treating methyl syn-2-hydroxyimino-2-(thien-2-yl)acetate with 1 equivalent of sodium methoxide) (1.0 g.) in benzene:dimethylformamide (2:1; 15 ml.) and the mixture was stirred for 17 hours at room temperature then poured into water. The aqueous solution was extracted with ethyl acetate, washed with water, dried and evaporated to give syn methyl ester (0.88 g) as a pale yellow oil.

2N-Sodium hydroxide (4.0 ml.) was added to a solution of the syn methyl ester (0.85 g.), in methanol (10 ml.) and the mixture was left at room temperature for 18 hr. The methanol was removed by evaporation, the aqueous residue was diluted with water, washed with ether and acidified to pH 2.0 with 2N-hydrochloric acid. The mixture was extracted with ethyl acetate, the combined extracts were washed with water, dried and evaporated to give the title compound (0.74 g., 81%) as a pale yellow oil, $\tau$ values (DMSO-$d_6$) include 2.30 2.7–3.0 (thien-2-yl protons), 5.84 (OCH$_2$), 9.10 (CH$_3$).

EXAMPLE 42

2-Methoxymethoxyimino-2-(thien-2-yl)acetic acid (syn-isomer)

A solution of sodium methoxide in methanol (approx. 0.2 M) was added to methyl 2-hydroxyimino-2-(thien-2-yl) acetate (syn-isomer) (0.5 g) and the solution formed was evaporated to a yellow oil which on azeotroping with petrol (b.p. 40°–60°) gave the sodium salt of methyl 2-hydroxyimino-2-(thien-2-yl) acetate (syn-isomer) (0.49 g., 88%). To a stirred solution of the sodium salt (0.49 g.) in benzene/DMF (5 mls., 2:1). was added chlorodimethyl ether (0.22 mls). After 10 mins. the reaction was poured into saturated sodium bicarbonate solution and extracted with benzene. The combined extracts were washed with water, dried over sodium sulphate and evaporated to a yellow oil, methyl 2-methoxymethoxyimino-2-(thien-2-yl) acetate (syn-isomer) (0.62 g; 100%) $\lambda_{max.\ (EtOH)}$ 288 nm ($\epsilon$ 10,300), $\nu_{max.}$ (CHBr$_3$) 1730 (COOCH$_3$), 1660 cm.$^{-1}$ (—C=N—), $\tau$ (CDCl$_3$) values include 2.61–2.83 (multiplet, thien-2-yl), 4.83 (singlet, CH$_2$), 6.06 (CO$_2$CH$_3$) 6.56 (singlet, CH$_2$OCH$_3$).

A solution of sodium hydroxide (4 ml. 2N) and methanol were added to the methyl ester (0.4 g.). After 30 mins. the reaction was poured into water and washed with ethyl acetate. The aqueous layer was acidified to pH 1 using 2N-hydrochloric acid and extracted with ethyl acetate. The ethyl acetate was dried and evaporated to a colorless oil which was azeotroped with petrol (bp. 40°–60°) to yield a white solid, syn 2-methoxymethoxyimino-2-(thien-2-yl)acetic acid (0.21 g; 55%), m.p. 61.2°, $\lambda_{max.}$ (EtOH) 286 nm ($\epsilon$ 10,400), $\nu_{max.}$ (Nujol) 1732, 2600 cm.$^{-1}$ (CO$_2$H), $\tau$ (DMSO-$d_6$) 2.26 (multiplet; thienyl H$_5$), 2.7–2.9 (multiplet, thienyl H$_3$ and H$_4$), 4.88 (singlet, O-CH$_2$—), 6.6 (singlet, OCH$_3$).

EXAMPLE 43

2-t-Butoxyimino-2-(benzo[b]-thien-2-yl)acetic acid (syn-isomer)

Benzo[b]-thien-2-ylglyoxylic acid (3.09 g) and t-butoxyamine hydrochloride (1.98 g) were dissolved in 50% aqueous ethanol (100 ml). The solution was adjusted to pH 4.5 with sodium hydroxide solution and maintained at such for 4 hr. at room temperature. Thin-layer chromatography showed incomplete reaction. t-Butoxyamine hydrochloride (500 mg.) was added and the solution kept at room temperature overnight. The alcohol was removed by evaporation and the aqueous phase adjusted to pH 8 and washed with ether. The aqueous phase was then acidified to pH 1.5 under ether. The ether solution was washed with water and dried. Evaporation gave a cream solid (4.05 g.). Fractional crystallisation from cyclohexane gave the anti-isomer of the title compound (1.6 g.). The mother liquors were combined and evaporated to give a cream solid (2.11 g.) that was treated in ether with excess diazomethane in ether at 0°–5°. The excess reagent was destroyed by acetic acid and the ether solution washed with sodium bicarbonate, water and dried. Evaporation gave an oil (1.75 g.). This was dissolved in methanol (70 ml) and treated with sodium hydroxide solution (N: 7 ml.) at room temperature for 3 hr. Hydrochloric acid (2N: 3.5 ml) was added and the methanol was removed by evaporation. The aqueous residue was partitioned between ether and sodium bicarbonate solution. The ether layer was washed with water and dried. Evaporation gave an oil (0.92 g.) that was dissolved in methanol (20 ml.) and treated with sodium hydroxide (N: 7 ml) at reflux temperature for 3hr. Sodium hydroxide (N: 5ml) was added and the solution refluxed for 6 hr. The methanol was removed by evaporation and the residue partitioned between ether and water. The aqueous phase was acidified (pH 1.5) under ether and the ether layer washed with water, dried and evaporated to give a pale orange crystalline solid (760 mg. 18%). Crystallisation from benzene containing cyclohexane gave syn-2-t-butoxyimino-2-(benzo[b]-thien-2-yl)acetic acid (430 mg.) m.p. 108°–9°, $\lambda_{max.}$ (EtOH) 231, 253, 297 nm ($\epsilon$17,000, 7,240, 24,500).

EXAMPLE 44

2-Isopropoxyimino-2-phenylacetic acid (syn isomer)

A mixture of phenylglyoxylic acid (3.0 g.), isopropoxyamine hydrochloride (2.5 g.), ethanol (100 ml) and water (50 ml) was stirred and adjusted to pH 4.5 to 5 with sodium hydroxide solution (2N). The solution was stirred for 5 hr. maintaining the pH at 4.5–5 with further additions of sodium hydroxide solution. The ethanol was removed by evaporation, the aqueous residue acidified and the product collected by extraction with ethyl acetate. Evaporation of the ethyl acetate gave a brown oil (4.2 g.). that was esterified conventionally with diazomethane to give a mixture of the syn and anti methyl esters of the title compound as an oil (4.04 g.).

The mixture of esters (4.0 g) in methanol (60 ml) was treated with sodium hydroxide solution (2N:19.0 ml) and kept for 2 hr. at room temperature. The methanol was evaporated and the residue, diluted with water, extracted with ethyl acetate. Evaporation of the dried (MgSO$_4$) ethyl acetate solution gave the crude syn methyl ester (0.82 g.). The ester (0.82 g) in methanol (20 ml) was treated with sodium hydroxide solution (2N:3.6 ml) and kept at room temperature for 31 hr. Conventional isolation of acidic material gave the crude syn isomer (0.706 g) which was recrystallised from cyclohexane to give the title compound (0.358 g.) m.p. 59.5° $\lambda_{max}$. (EtOH) 258 nm ($\epsilon$ 12,700), $\tau$ (DMSO-d$_6$) values include 2.47 (phenyl), 5.53 (O-CH<), 8.71 (CH$_3$).

EXAMPLE 45

2-n-Propoxyimino-2-(thien-2-yl)acetic acid (syn isomer)

A mixture of thien-2-ylglyoxylic acid (3.12 g), n-propoxyamine hydrochloride (2.8 g.), ethanol (75 ml) and water (75 ml) was adjusted to pH 4.5 to 5 with sodium hydroxide solution (2N) and stirred at room temperature. A clear solution at pH 4.5 to 5 was maintained by further additions of base and ethanol as required. After 4 hr. a further portion of n-propoxyamine hydrochloride (1.4 g) was added and the mixture stirred for a further 3 hr. (keeping the pH at 4.5–5) and then kept overnight. The ethanol was evaporated and the residual solution diluted with water, acidified and extracted with ethyl acetate. Evaporation of the dried (MgSO$_4$) ethyl acetate solution gave a mixture of the syn and anti forms of the title acid as an oil (4.8 g.).

The mixture of acids was esterified conventionally with diazomethane to give a mixture of the syn and anti methyl ester (3.175 g.).

The mixtures of esters in methanol (50 ml.) was treated with sodium hydroxide solution (2N; 14 ml) for 10 min. at room temperature. The methanol was removed, rapidly, by evaporation and the residue, in water, extracted with ethyl acetate. Evaporation of the dried (MgSO$_4$) ethyl acetate solution gave the syn methyl ester (0.416 g). The ester in methanol (10 ml) was treated with sodium hydroxide solution (2N: 1.7 ml) and kept at room temperature for 26 hr. Conventional isolation of acid material gave the title compound as an oil (0.235 g.) $\tau$ (DMSO-d$_6$) values include 2.28, 2.7–2.9 (thienyl), 5.90 (O—CH$_2$).

EXAMPLE 46

2-Phenoxyimino-2-phenylacetic acid (syn- isomer)

A solution of syn-2-hydroxyimino-2-phenylacetic acid (33 g) in dry methanol (500 ml) was treated with 1.105 N sodium methoxide solution (486 ml), and stirred for 15 minutes. To the solution was added diphenyliodonium bromide (90 g), and the resulting mixture was stirred for 18 hours under nitrogen. A small amount of solid was filtered off, and the filtrate was evaporated to dryness. Water (600 ml) and ether (600 ml) were added to the residue, and the pH of the mixture was adjusted to 7.0 with concentrated hydrochloric acid. The aqueous layer was washed twice with ether, and then acidified under ether to pH 1.8 with concentrated hydrochloric acid. The acid mixture was extracted into ether, and the combined extracts were washed (water, saturated brine), dried, and evaporated to give a dark brown solid (ca 35 g). This solid was triturated with ice-cold nitromethane. The solid was collected, washed with a little cold nitromethane, and dried in vacuo to give fawn crystals of the title acid (24.41 g, 51%), m.p. 104°–105.1°, $\epsilon_{max}$. (ethanol) 267.5, 285 nm ($\epsilon$11,600; 10,100). Similarly were prepared:-

EXAMPLE 47

2-Phenoxyimino-2-(thien-2-yl)acetic acid (synisomer) (52%) m.p. 98.3°–99.5°, $\lambda_{max}$. (ethanol) 267.5, 303 nm. ($\epsilon$ 9,900; 12,000). and

EXAMPLE 48

2-Phenoxyimino-2-(fur-2-yl)acetic acid (synisomer) (34%), m.p. 100.7°–100.9°, $\lambda_{max}$. (ethanol) 270.5, 292.5 nm ($\epsilon$ 14.300; 15,700).

EXAMPLE 49

2-Cyclopentyloxyimino-2-(fur-2-yl)acetic acid (synisomer)

Fur-2-yl glyoxylic acid (2.80 g) and cyclopentyloxyamine hydrochloride (3.3 g) were dissolved in a mixture of water (100 ml) and ethanol (50 ml), and the pH of the solution was adjusted to 5.0. The solution was stirred for 19 hours, the alcohol was evaporated off, and the solution was acidified to pH of 1.5 under ethyl acetate. The acid mixture was extracted into ethyl acetate, and the combined extracts were washed, dried, and evaporated to give the crude acid (4.38 g). This acid was treated with charcoal in benzene for 15 minutes, filtered, and the filtrate was evaporated to give a solid which was recrystallised twice from cyclohexane to give the title acid (2.28 g, 51%), m.p. 96.6°–97.7°, $\lambda_{max}$. (ethanol) 277.5 nm ($\epsilon$ 15,600).

EXAMPLE 50

2-(Thien-2-ylmethoxyimino)-2-(1-methylpyrrol-2-yl)acetic acid (syn-isomer)

A solution of 1-methylpyrrol-2-ylglyoxylic acid (4.6 g) and thien-2-ylmethoxyamine hydrochloride (5.46 g) in aqueous ethanol (100 ml, 1:1) was adjusted to pH 4.8 with 10N-sodium hydroxide solution and stirred at pH 4.8 for 24 hours at room temperature. A further portion of thien-2-ylmethoxamine (0.5 g) was added and the solution was maintained at pH 4.8 and room temperature for a further 2 days. The pH was then adjusted to 8 with sodium bicarbonate solution and the ethanol was removed by evaporation. The aqueous residue was washed with ether and the aqueous phase was acidified to pH 1.5 under ether with 2N-hydrochloric acid. The ether extracts were combined and washed with water, dried and evaporated to give an orange oil (8.8 g). The crude mixture of syn and anti-isomer was esterified with a slight excess of diazomethane in ether.

To a solution of the mixed methyl esters (7.7 g) in methanol (100 ml) was added N-sodium hydroxide (28 ml). The mixture was kept at room temperature for 3 hours when thin-layer chromatography of an aliquot showed only traces of remaining anti-ester. After a further 30 minutes 2N-hydrochloric acid (14 ml) was added and the methanol was removed by evaporation. The residue was partitioned between ether and excess sodium bicarbonate in water. The ether layer was separated, washed with water, dried and evaporated to a pale orange oil (5.9 g).

This oil in methanol (100 ml) was treated with 10N-sodium hydroxide solution (4.5 ml) and kept at room temperature for 16 hours. A further portion of 10N-sodium hydroxide solution (4.5 ml) was added and after 24 hours at room temperature the mixture was warmed to 60° for 30 minutes. The methanol was removed by evaporation and the residue divided between ether and sodium bicarbonate solution. The aqueous phase was acidified under ether with 2N-hydrochloric acid. The combined ether extracts were washed with water and dried. Evaporation of the ether gave a plae orange oil (4.8 g) which was crystallised from carbon tetrachloride to give the title compound as pale brown crystals (1.9 g); m.p. 70°–71°; $\frac{1}{3}_{max.}$ (EtOH) 235, 287.5 nm ($\epsilon$ 11,600 and 17,100); $\tau$ (DMSO-$d_6$) values include 4.70 (S, $CH_2$) and 6.18 (S, $CH_3$).

EXAMPLE 51

2-Methoxyimino-2-phenylacetyl chloride (syn isomer)

Phosphorous pentachloride (5.21 g) was added in portions to a stirred suspension of syn-2-methoxyimino-2-phenylacetic acid (4.51 g. in dry benzene (20 ml.). Thionyl chloride (0.3 ml) was added to the solution, which was refluxed for 30 minutes. Benzene was removed by evaporation, and the residue distilled, producing a mixture of syn- and anti-acid chlorides (ca. 1:1) as a colourless oil (3.08 g., 62%), b.p. 74° (0.01 mm). A repeat of this reaction (on 5.04 mmole) at room temperature also produced a mixture of the isomeric acid chlorides.

The acid chlorides were separated and purified by preparative plate chromatography, developing three times with petroleum spirit (b.p. 60°–80°) producing the title compound as a colourless oil (1.43 g. 24%).

In a further experiment a mixture of syn- and anti-2-methoxyimino-2-phenylacetic acids (10 g., ca 1:1) were converted to a mixture of acid chlorides as above and chromatographed on silica gel (120 g., Hopkins and Williams, MFC) using petroleum spirit (b.p. 60°–80°) to give the title compound (4.32 g., 39%).

EXAMPLE 52

General Method for Converting a 2-Alkoxyimino-2-arylacetic Acid into its Acid Chloride without Isomerisation A solution of the pure syn- 2-(substituted oxyimino)-2-arylacetic acid (1 equiv.) in methanol (ca. 2–4 ml./mmole.) is treated with sodium methoxide (1 equiv.) in methanol at 0°–25° and the mixture evaporated to give the sodium salt which may be dried by azeotroping with several portions of benzene and/or drying in vacuo over phosphorus pentoxide.

The anhydrous sodium salt (1 equiv.) is suspended in dry benzene (ca. 5 ml/mmole) containing a few drops of dry dimethylformamide and treated with freshly distilled oxalyl chloride (1–2.5 equiv). The mixture is stirred at room temperature for 1 hr and then evaporated to remove benzene.

The following acids were converted into their acid chlorides in this way:

Syn-2-Ethoxyimino-2-phenylacetic acid,
Syn-2-t-Butoxyimino-2-phenylacetic acid,
Syn-2-Benzyloxyimino-2-phenylacetic acid,
Syn-2-(Thien-2-ylmethoxyimino)-2-phenylacetic acid,
Syn-2-Methoxyimino-2-(thien-2-yl)acetic acid,
Syn-2-Ethoxyimino-2-(thien-2-yl)acetic acid,
Syn-2-n-Butoxyimino-2-(thien-2-yl)acetic acid,
Syn-2-t-Butoxyimino-2-(thien-2-yl)-acetic acid,
Syn-2-(2bromoethoxyimino)-2-(thien-2-yl)acetic acid,
Syn-2-(2-t-Butoxycarbonylaminoethoxyimino)-2-(thien-2-yl)acetic acid,
Syn-2-Benzyloxyimino-2-(thien-2-yl)acetic acid,
Syn-2-(Thien-2-ylmethoxyimino)-2-(thien-2-yl)-acetic acid,
Syn-2-(1-Ethoxyethoxyimino)-2-(thien-2-yl)acetic acid,
Syn-2-(Pyrid-2-ylmethoxyimino)-2-(thien-2-yl)acetic acid,
Syn-2-Methoxyimino-2-(naphth-1-yl)acetic acid,
Syn-2-t-Butoxyimino-2-(naphth-1-yl)acetic acid,
Syn-2-Benzyloxyimino-2-(naphth-1-yl)acetic acid,
Syn-2-Methoxyimino-2-(benzo[b]-thien-3-yl)acetic acid,
Syn-2-t-Butoxyimino-2-(benzo[b]-thien-3-yl)acetic acid,
Syn-2-Benzyloxyimino-2-(benzo[b]-thien-3-yl)acetic acid,
Syn-2-Methoxyimino-2-(benzo[b]-thien-2-yl)acetic acid,
Syn-2-t-Butoxyimino-2-(benzo[b]-thien-2-yl)acetic acid,
Syn-2-Butoxyimino-2-(benzo[b]-thien-2-yl)acetic acid,
Syn-2-Methoxyimino-2-(fur-2-yl)acetic acid,
Syn-2-t-Butoxyimino-2-(fur-2-yl)acetic acid,
Syn-2-Benzyloxyimino-2-(fur-2-yl)acetic acid,
Syn-2-(Fur-2-ylmethoxyimino)-2-(fur-2-yl)acetic acid,
Syn-2-Ethoxyimino-2-(fur-2-yl)acetic acid,
Syn-2-n-Butoxyimino-2-phenylacetic acid,
Syn-2-Isopropoxyimino-2-phenylacetic acid,
Syn-2-n-Propoxyimino-2-phenylacetic acid,
Syn-2-n-Propoxyimino-2-(thien-2-yl)acetic acid,
Syn-2-Ethoxyimino-2-(benzo[b]-fur-2-yl)acetic acid,
Syn-2-Ethoxyimino-2-(thien-3-yl)acetic acid,
Syn-2-phenoxyimino-2-phenylacetic acid,
Syn-2-Phenoxyimino-2-(thien-2-yl)acetic acid,
Syn-2-Phenoxyimino-2-(fur-2-yl) acetic acid,
Syn-2-Cyclopentyloxyimino-2-(fur-2-yl)acetic acid,
Syn-2-cyclopentyloxyimino-2-(thien-2-yl)acetic acid,
Syn-2-t-Butoxyimino-2-(benzo[b]fur-2-yl)acetic acid,
Syn-2-Methoxyimino-2-(1-methylpyrrol-2-yl)acetic acid,
Syn-2-t-Butoxyimino-2-(1-methylpyrrol-2-yl)acetic acid,
Syn-2-Cyclopentyloxyimino-2-phenylacetic acid,
Syn-2-Methoxyimino-2-(1-benzyloxymethylpyrrol-2-yl)acetic acid,
Syn-2-t-Butoxycarbonylmethoxyimino-2-phenylacetic acid, and
Syn-2-(Thien-2-ylmethoxyimino)-2-(1-methylpyrrol-2-yl) acetic acid.

We claim:

1. A compound selected from the group consisting of an acid of the formula

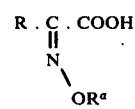

wherein R is thienyl; furyl; benzothienyl; benzofuryl; or thienyl, furyl, benzothienyl or benzofuryl substituted by fluoro, chloro, bromo, iodo, hydroxy, lower alkyl, nitro, amino, lower alkylamino, di(lower alkyl)amino, lower alkanoyl, lower alkanoylamido, lower alkoxy, lower alkylthio or carbamoyl; and $R^a$ is lower alkyl; lower cycloalkyl; phenyl; naphthyl; benzyl; phenylethyl; diphenylmethyl; triphenylmethyl; thienylmethyl;

furylmethyl; pyridylmethyl; pyrrolylmethyl; or any of these groups substituted by hydroxy, carboxy, lower alkxoycarbonyl, benzyloxycarbonyl, acetamido, benzamido, cyano, lower alkanoyl, amino, lower alkoxycarbonylamino, benzyloxycarbonylamino, fluoro, chloro, bromo, iodo or lower alkoxy, the said acid being in the form of a syn isomer free of the corresponding anti isomer to the extent of at least 75% based on the total weight of said acid; and the acid chloride thereof.

2. The compound of claim 1 which is syn-2-methoxyimino-2-(thien-2-yl)acetic acid.

3. The compound of claim 1 which is syn-2-ethoxyimino-2-(thien-2-yl)acetic acid.

4. The compound of claim 1 which is syn-2-n-propoxyimino-2-(thien-2-yl)acetic acid.

5. The compound of claim 1 which is syn-2-n-butoxyimino-2-(thien-2-yl)acetic acid.

6. The compound of claim 1 which is syn-2-t-butoxyimino-2-(thien-2-yl)acetic acid.

7. The compound of claim 1 which is syn-2-cyclopentyloxyimino-2-(thien-2yl)acetic acid.

8. The compound of claim 1 which is syn-2-phenoxyimino-2-(thien-2-yl)acetic acid.

9. The compound of claim 1 which is syn-2-methoxyimino-2-(fur-2-yl)acetic acid.

10. The compound of claim 1 which is syn-2-ethoxyimino-2-(fur-2-yl)acetic acid.

11. The compound of claim 1 which is syn-2-t-butoxyimino-2-(fur-2-yl)acetic acid.

12. The compound of claim 1 which is syn-2-cyclopentyloxyimino-2-(fur-2-yl)acetic acid.

13. The compound of claim 1 which is syn-2-phenoxyimino-2-(fur-2-yl)acetic acid.

14. The compound of claim 1 which is syn-2-methoxyimino-2-(fur-2-yl)acetyl chloride.

15. The compounds of claim 1 which is syn-methoxyimino-2-(thien-2-yl)acetyl chloride.

* * * * *